(12) United States Patent
Segal

(10) Patent No.: US 9,913,808 B2
(45) Date of Patent: Mar. 13, 2018

(54) INJECTABLE PHARMACEUTICAL COMPOSITIONS FOR THE TREATMENT OF JOINTS

(76) Inventor: David Segal, Tel Aviv (IL)

(*) Notice: Subject to any disclaimer, the term of this patent is extended or adjusted under 35 U.S.C. 154(b) by 0 days.

(21) Appl. No.: 13/807,545

(22) PCT Filed: Jun. 15, 2011

(86) PCT No.: PCT/IL2011/000495
§ 371 (c)(1),
(2), (4) Date: Dec. 28, 2012

(87) PCT Pub. No.: WO2012/001679
PCT Pub. Date: Jan. 5, 2012

(65) Prior Publication Data
US 2013/0289131 A1    Oct. 31, 2013

(30) Foreign Application Priority Data

Jun. 30, 2010 (IL) .......................................... 206739

(51) Int. Cl.
| | |
|---|---|
| A61K 9/00 | (2006.01) |
| A61K 31/047 | (2006.01) |
| A61K 45/06 | (2006.01) |
| A61L 27/20 | (2006.01) |
| A61L 27/54 | (2006.01) |
| A61K 31/196 | (2006.01) |
| A61K 31/573 | (2006.01) |
| A61K 31/728 | (2006.01) |
| A61K 47/36 | (2006.01) |

(52) U.S. Cl.
CPC .......... *A61K 31/047* (2013.01); *A61K 9/0019* (2013.01); *A61K 31/196* (2013.01); *A61K 31/573* (2013.01); *A61K 31/728* (2013.01); *A61K 45/06* (2013.01); *A61K 47/36* (2013.01); *A61L 27/20* (2013.01); *A61L 27/54* (2013.01); *A61L 2300/216* (2013.01); *A61L 2300/41* (2013.01); *A61L 2300/428* (2013.01); *A61L 2300/45* (2013.01); *A61L 2400/06* (2013.01); *A61L 2430/24* (2013.01)

(58) Field of Classification Search
None
See application file for complete search history.

(56) References Cited

U.S. PATENT DOCUMENTS

| | | | |
|---|---|---|---|
| 4,767,785 A * | 8/1988 | Georgieff ....................... 514/561 |
| 4,957,744 A | 9/1990 | della Valle et al. |
| 5,095,037 A * | 3/1992 | Iwamitsu et al. ............. 514/561 |
| 5,510,418 A | 4/1996 | Rhee et al. |
| 6,068,614 A * | 5/2000 | Kimber ................. A61M 5/178 264/478 |
| 6,716,819 B2 * | 4/2004 | Welsh .................. A61K 31/047 514/23 |
| 6,733,753 B2 | 5/2004 | Boone et al. |
| 7,296,566 B2 * | 11/2007 | Alchas .................. A61M 15/08 128/200.14 |
| 2005/0148597 A1 * | 7/2005 | Kostanski ............ A61K 9/0019 514/253.07 |
| 2010/0136140 A1 * | 6/2010 | Zhao ............................ 424/680 |
| 2011/0201571 A1 | 8/2011 | Gavard Molliard |

FOREIGN PATENT DOCUMENTS

| | | |
|---|---|---|
| JP | 3236330 A | 10/1991 |
| WO | 2010/052430 A2 | 5/2010 |
| WO | 2012/143876 A1 | 10/2012 |

OTHER PUBLICATIONS

Ferguson et al. Rheologica Acta 10, 15-20 (1971).*
"Definition isotonic" in www.google.com/search?q=frinition+isotonic&sourceid=ie 7&rls=com.microsoft:en-us:IE-Address&ie=&oe= (retrieved from the internet Feb. 1, 2014).*
Donohoe et al. In Journal of Clinical Pharmacology (1974) 14, 255-260.*
2007 Guideline for Isolation Precaution: Preventing Transmissions of Infectious Agents in Healthcare Settings at www.cdc.gov/hicpac/pdf/isolation/Isolation2007.pdf. (retrieved from the internet on Oct. 23, 2014).*
Nandi et al. in Toxicology (2005) 26-35.*
Durairaj et al. in Respiratory Research 2004 5:13.*
Hydralyte Sports at http://hydralytesports.com.au/isotonic-vs-hypotonic/page (retireved from the internet, May 10, 2016).*
Milgrom et al. in International Journal of Pediatric Otorhinolaryngology 71, 89-94 (2007).*
Kopalli et al. in Neurotoxicity 34:25-32 (2013) (Abstract).*
Vernacchio et al. in International Journal of Pediatric Otorhinolaryngology 71, 89-94 (2007).*
Kohlmeier, M. in Nutrient Metabolism, Structure, Function and Genes 2nd Ed. (2015).*
Milgrom et al. in Arch. Pediatr. Adolesc. Med 2009; 163(7):601-607.*
'Isotonic' at https://www.google.com/search?q=isotonic&sourceid=ie7&rls=com.microsoft:en-US:IE-Address&ie=&oe= (retrieved from the internet on Jan. 5, 2017).*
Health Benefits of Plums at https://www.organicfacts.net/health-benefits/fruit/health-benefits-of-plums.html (retrieved from the Internet on Jan. 5, 2017).*
PCT/IL2011/000495, International Search Report dated Nov. 30, 2011, 1 p.
PCT/IL2011/000495, Written Opinion dated Nov. 30, 2011, 5 pp.
Merkher et al., "A rational human joint friction test using a human cartilage-on-cartilage arrangement" Tribology Letters (2006) vol. 22, No. 1, pp. 29-36.

(Continued)

*Primary Examiner* — Dennis Heyer
(74) *Attorney, Agent, or Firm* — Sterne, Kessler, Goldstein & Fox P.L.L.C.

(57) ABSTRACT

The present invention relates to an injectable pharmaceutical formulation for the alleviation or reduction of joint irritation or for the reduction of worsening of existing joint inflammation, formulated for intra-articular injection comprising an active polyol ingredient, which polyol active ingredient is xylitol. Use of the intra-articular injectable formulations for the treatment of joint diseases or conditions including arthritis is described.

20 Claims, No Drawings

(56) References Cited

OTHER PUBLICATIONS

Tichy et al., "The Phan-Thien and tanner model applied to thin film spherical coordinates: Applications for lubrication of hip joint replacement" Journal of Biomechanical Engineering (2008) vol. 130, pp. 21012-1-21012-6.

Donahoe et al., "Xylitol—Clinical Pharmacology in Normal Adult Volunteers" Journal of Clinical Pharmacology (1974) vol. 14, pp. 255-260.

Eisenberg et al., "Studies on the Glucuronic Acid Pathway of Glucose Metabolism" J. Biol. Chem. (1959) vol. 234, pp. 250-253.

Frank, "Anwendung von Kohlehydraten in der neuzeitllche Infusionstheraple unter Berucksichtigung von Xylit" Die Krankenhaus-Apotheke (1970) vol. 3, pp. 14-16.

Frank, "Anwendung von Kohlehydraten in der neuzeitllche Infusionstheraple unter Berucksichtigung von Xylit" Die Krankenhaus-Apotheke (1970) vol. 3, pp. 14-16. Unofficial Google English translation of the following portions: title; p. 14, col. 2, lines 18-31; and p. 16, col. 1, line 6 to the end of the text of the article—two pages of Google translation provided.

Wang et al., "Short Synthesis of 3-(Hydroxymethyl)xylitol and Structure Revision of the Anti-diabetic Natural Product from Casearia esculenta" Organic Letters (2013) vol. 15, No. 21, pp. 5610-5612.

AAOS clinical practice guideline, "Treatment of Osteoarthritis of the Knee" 2nd edition, Summary of Recommendations (May 18, 2013), http://www.aaos.org/Research/guidelines/OAKSummaryofRecommendations.pdf (24 pages) last accessed Jul. 28, 2015.

AAOS clinical practice guideline, Recommendation 9 in "Treatment of Osteoarthritis of the Knee" 2nd edition (May 18, 2013), http://www.aaos.org/Research/guidelines/TreatmentofOsteoarthritisoftheKneeGuideline.pdf (102 pages) last accessed Jul. 28, 2015.

Cardone et al., "Diagnostic and Therapeutic Injection of the Hip and Knee" American Family Physician (2003) vol. 67, No. 10, pp. 2147-2152.

Courtney et al., "Joint aspiration and injection and synovial fluid analysis" Best Practice & Research Clinical Rheumatology (2013) vol. 27, pp. 137-169.

Hakshur et al., "The effect of hyaluronan injections into human knees on the number of bone and cartilage wear particles captured by bio-ferrography" Acta Biomaterialia (2011) vol. 7, pp. 848-857.

Han et al., "Xylitol Inhibits Inflammatory Cytokine Expression Induced by Lipopolysaccharide from Porphyromonas gingivalis" Clinical and Diagnostic Laboratory Immunology (2005) vol. 12, No. 11, pp. 1285-1291.

Hansen et al., "Double Lavage Technique for Determination of Synovial Fluid Volume and Constituent Concentrations" ORS 2011 Annual Meeting—Poster No. 2046 (1 page).

Kaivosoja et al., "Dietary xylitol protects against the imbalance in bone metabolism during the early phase of collagen type II-induced arthritis in dark agouti rats" Metabolism Clinical and Experimental (2008) vol. 57, pp. 1052-1055.

Korponyai et al., "Antiirritant Properties of Polyols and Amino Acids" Dermatitis (2011) vol. 22, No. 3, pp. 141-146.

Kraus et al., "Brief report—Measurement of synovial fluid volume using urea" OsteoArthritis and Cartilage (2007) vol. 15, pp. 1217-1220.

Kusayama et al., "Changes in synovial fluid biomarkers and clinical efficacy of intra-articular injections of hyaluronic acid for patients with knee osteoarthritis" Journal of Experimental Orthopaedics (2014) vol. 1, Article 16 (9 pages).

Lockman, "Knee Joint Injections and Aspirations—the triangle technique" Canadian Family Physician (2006) vol. 52, pp. 1403-1404.

Mattila et al., "Dietary Xylitol Protects Against Weakening of Bone Biomechanical Properties in Ovariectomized Rats" J. Nutr. (1998) vol. 128, No. 10, pp. 1811-1814.

Ostergaard et al., "Quantitative Assessment of the Synovial Membrane in the Rheumatoid Wrist: an Easily Obtained MRI Score Reflects the Synovial Volume" British Journal of Rheumatology (1996) vol. 35, pp. 965-971.

Raynauld et al., "Safety and Efficacy of Long-Term Intraarticular Steroid Injections in Osteoarthritis of the Knee" Arthritis & Rheumatism (2003) vol. 48, No. 2, pp. 370-377.

Smith et al., "Effect of Intra-Articular HA Injection on the Synovial Fluid of OA Joints" 46th Annual Meeting, Orthopaedic Research Society, Mar. 12-15, 2000, Orlando, Florida—Session 39—Osteoarthritis I, p. 0233.

Suplasyn—Product Overview—Bionichepharma, Geneva, Switzerland (2010) 2 pages.

Torry et al., "The Effects of Knee Joint Effusion on Quadriceps Electromyography During Jogging" Journal of Sports Science and Medicine (2005) vol. 4, pp. 1-8.

Excerpted file history, U.S. Appl. No. 15/400,370: $1^{st}$ preliminary amendment filed Jan. 6, 2017; $2^{nd}$ preliminary amendment filed Jan. 9, 2017; election of species requirement dated Feb. 9, 2017; reply and $3^{rd}$ preliminary amendment filed Apr. 10, 2017; and Notice of Allowance and Issue Fee Due dated May 5, 2017; United States Patent and Trademark Office, Alexandria, VA.

\* cited by examiner

INJECTABLE PHARMACEUTICAL COMPOSITIONS FOR THE TREATMENT OF JOINTS

CROSS-REFERENCE TO RELATED APPLICATIONS

This application is a National Stage Entry of International Application No. PCT/IL2011/000495, filed Jun. 22, 2011, which claims priority to IL Patent Application No. 206739, filed Jun. 30, 2010.

FIELD OF THE INVENTION

The present invention relates to an injectable pharmaceutical formulation for the alleviation or reduction of joint irritation or for the reduction of worsening of existing joint inflammation, formulated for intra-articular injection.

BACKGROUND OF THE INVENTION

Articular and/or joint cartilage damages are injuries or lesions caused by various means, such as ageing, mechanical, chemical, viral, bacterial, fungal and other pathogenic organisms, which affects joint tissue structures. The result is pain, swelling or both.

Wound repair consists of a series of processes whereby injured tissue is repaired, inflammation or irritation is reduced, specialized tissue is regenerated, and new tissue is reorganized partially or completely and clinical improvements are observed.

Tissue repair is a dynamic pathway that affects tissue integrity and function. Tissue repairing pathways are set into motion at the moment of tissue damage or irritation. Tissue repairing is the result of the accumulation of processes, including inflammation, ground substance and matrix synthesis, angiogenesis, fibroplasia, epithelialization, remodeling and influences tissue and cellular biochemistry.

DESCRIPTION OF THE INVENTION

It is an object of the present invention to provide an injectable pharmaceutical formulation for the alleviation or reduction of joint irritation or inflammation, for the alleviation or reduction of or for the reduction of worsening of existing joint inflammation as a result of further irritation, or for the alleviation or reduction of arthritis, formulated for intra-articular injection.

More particularly, according to the present invention, there is now provided an injectable pharmaceutical formulation for the prevention of joint irritation or worsening of existing joint inflammation as a result of further irritation, formulated for intra-articular injection, comprising Xylitol as active ingredient therein.

In some embodiments, this invention provides an injectable pharmaceutical formulation for the alleviation or reduction of joint irritation or for the reduction of worsening of existing joint inflammation as a result of further irritation, formulated for intra-articular injection, comprising an active polyol ingredient, which polyol active ingredient is Xylitol.

In some embodiments of the present invention the Xylitol is D-xylitol. In some embodiments of the present invention the Xylitol is L-xylitol or in some embodiments, the xylitol is D,L-xylitol.

In some embodiments of the present invention said concentration of Xylitol is between 0.5% and 10% in water.

In some embodiments said pharmaceutical formulation contains at least one polymer.

In some embodiments of the present invention said pharmaceutical formulation further comprises an anionic polymer with molecular weight higher than 500,000 dalton in order to provide the formulation with non-newtonian shear thinning viscosity.

It is known that anionic polymers such as sodium hyaluronate in the presence of inorganic salts such as phosphate buffer, exhibit a Newtonian viscosity profile.

The Advantage of a non-newtonian shear thinning viscosity profile is that when force is applied to the same, the viscosity immediately and precipitously drops. In accordance with this, when the stickiness between two pieces of human cartilage was measured in vitro with 1% sodium hyaluronate between them, the non-Newtonian (salt free) formulation was less sticky than the usual formulations.

In 24 measurements (Load: 10N, speed of movement 1 mm/sec., temperature 36-37° C.) the dynamic viscosity coefficient of the non-Newtonian (isotonicity by polyol) formulation was 0.03759±0.01481, whereas the dynamic viscosity of the Newtonian formulation (isotonicity by 0.9% sodium chloride) was 0.04892±0.01370, namely, more sticky. In some embodiments of the present invention the concentration of neutralized hyaluronic acid is 0.1% to 5%.

In one embodiment of the present invention said anionic polymer is in the form of a salt thereof and said formulation contains less than 0.01% of any inorganic salt.

In some embodiments of the present invention said pharmaceutical formulation is substantially devoid of any oil in water or wax in water emulsion.

In other embodiments of the present invention said Xylitol is in isotonic concentration.

In other embodiments, said pharmaceutical formulation further comprises at least one pharmaceutically acceptable excipient or additive.

In other embodiments said pharmaceutical formulation further comprises at least one further pharmaceutical agent selected from the group consisting of an anti-inflammatory agent, an antioxidant, a vitamin, another polyol and combinations thereof.

In one embodiment, the composition further comprises an anti-inflammatory agent such as betamethasone, prednisolone, piroxicam, aspirin, flurbiprofen and (+)-N-{4-[3-(4-fluorophenoxy)phenoxy]-2-cyclopenten-1-yl}-N-hyroxyurea salsalate, diflunisal, ibuprofen, fenoprofen, fenamate, ketoprofen, nabumetone, naproxen, diclofenac, indomethacin, sulindac, tolmetin, etodolac, ketorolac, oxaprozin, or celecoxib; an antiviral such as acyclovir, nelfinavir, or virazole; an antibiotic such as ampicillin and penicillin G or belonging to the family of penicillines, cephalosporins, aminoglycosidics, macrolides, carbapenem and penem, beta-lactam monocyclic, inhibitors of beta-lactamases, tetracyclins, polipeptidic antibiotics, chloramphenicol and derivatives, fusidic acid, lincomicyn, novobiocine, spectinomycin, poly-etheric ionophores, quinolones; an anti-infective such as benzalkonium chloride or chlorhexidine; dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin including penicillin G and penicillin V, ticarcillin rifampin and tetracycline; an antiinflammatory such as diflunisal, ibuprofen, indomethacin, meclofenamate, mefenamic acid, naproxen, oxyphenbutazone, phenylbutazone, piroxicam, sulindac, tolmetin, aspirin and salicylates, phytosphingosine type agents or a combination thereof.

In one embodiment, the composition further comprises a steroid. In one embodiment, the term "steroid" refers to naturally occurring steroids and their derivatives as well as synthetic or semi-synthetic steroid analogues having steroid-like activity. In one embodiment, the steroid is a glucocorticoid or corticosteroid. For example, many such steroids have a core fused ring structure based on cyclopentanophenanthrene. Examples of specific natural and synthetic steroids include, but are not limited to: aldosterone, beclomethasone, betamethasone, budesonide, cloprednol, cortisone, cortivazol, deoxycortone, desonide, desoximetasone, dexamethasone, difluorocortolone, fluclorolone, flumethasone, flunisolide, fluocinolone, fluocinonide, fluocortin butyl, fluorocortisone, fluorocortolone, fluorometholone, flurandrenolone, fluticasone, halcinonide, hydrocortisone, icomethasone, meprednisone, 25 methylprednisolone, paramethasone, prednisolone, prednisone, tixocortol or triamcinolone, and their respective pharmaceutically acceptable salts or derivatives. It will be appreciated that combinations of such steroids may also be used in accordance with this invention.

In other embodiments, the present invention is directed to the use of Xylitol in the manufacture of an injectable pharmaceutical formulation, formulated for intra-articular injection, for the alleviation or reduction of joint irritation or of the worsening of existing joint inflammation.

While Xyliltol is known in the prior art as a topical anti-irritant, it could not be predicted, nor was it obvious, that it would be effective for the prevention of joint irritation or worsening of existing joint inflammation when formulated for intra-articular injection. This is especially so since the joints of the body are known to be different than all other structures in the body in that they are lined with synovial membranes and are the only structures in the body having hyaline cartilage.

Furthermore, as is known, joints exhibit a different rate of absorption than any other structure in the body and therefore the effect of a specific compound on the joints cannot be learned from the effect of said compound elsewhere in the body.

For alleviating or reducing irritation or the worsening of existing joint inflammation, the preferred formulation might contain a polymer for example: Carbomer, Hyaluronate, Carboxy Methyl Cellulose, hydroxyl propyl methyl cellulose, polyvinyl alcohol or similar. To achieve non-newtonian property of the injection, an anionic polymer is used and as stated above, the formulation will not contain any significant concentration of an inorganic salt, other than the salt of said anionic polymer, in order to prevent interference with the property of non-newtonian shear thinning viscosity.

One embodied method to achieve non-newtonian shear thinning viscosity property is to inject a preparation with isotonic xylitol and 1% sodium Hyaluronate.

The sterile solution might be portioned in vials or in single injections or any other convenient way for practical use.

In some embodiments, the term "contacting" or "administering" refers to both direct and indirect exposure to the indicated material.

In some embodiments, the compositions and/or methods of this invention comprise or make use of a non-sterile or sterile carrier or carriers for administration to cells, tissues or organisms, such as a pharmaceutical carrier suitable for administration to an individual. Such carriers may include, but are not limited to, saline, buffered saline, dextrose, water, glycerol, and combinations thereof.

In some embodiments, the compositions and/or methods of this invention comprise or make use of pharmaceutically acceptable carriers, which may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

In addition, the compositions of this invention may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweeteners (e.g., aspartame, citric acid), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

Solid carriers/diluents include, but are not limited to, a gum, a starch (e.g., corn starch, pregeletanized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof.

In one embodiment, compositions of this invention are pharmaceutically acceptable. In one embodiment, the term "pharmaceutically acceptable" refers to any formulation which is safe, and provides the appropriate delivery for the desired route of administration of an effective amount of at least one compound for use in the present invention. This term refers to the use of buffered formulations as well, wherein the pH is maintained at a particular desired value, ranging from pH 4.0 to pH 9.0, in accordance with the stability of the compounds and route of administration.

In one embodiment, suitable pharmaceutically acceptable carriers include but are not limited to water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, white paraffin, glycerol, alginates, hyaluronic acid, collagen, perfume oil, fatty acid monoglycerides and diglycerides, pentaerythritol fatty acid esters, hydroxy methylcellulose, polyvinyl pyrrolidone, etc. In another embodiment, the pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. In another embodiment, they can also be combined where desired with other active agents, e.g., vitamins.

It will be apparent to those skilled in the art that various modifications and variations can be made in the compositions, use and preparations of the present invention without departing from the spirit or scope of the invention.

For administration to mammals, and particularly humans, it is expected that in the case of medications, the physician or other qualified healthcare provider may determine the actual dosage and duration of treatment, which will be most suitable for an individual and can vary with the age, weight and response of the particular individual.

In some embodiments, any of the compositions of this invention will comprise an active polyol ingredient, which polyol active ingredient is Xylitol in any form or embodiment as described herein. In some embodiments, any of the compositions of this invention will consist of an active polyol ingredient, which polyol active ingredient is Xylitol, in any form or embodiment as described herein. In some embodiments, any of the compositions of this invention will consist essentially of an active polyol ingredient, which polyol active ingredient is Xylitol, in any form or embodiment as described herein.

In some embodiments, the term "comprise" refers to the inclusion of the indicated active agent, such as the Xylitol, as well as inclusion of other active agents, and pharmaceutically acceptable carriers, excipients, emollients, stabilizers, etc., as are known in the pharmaceutical industry.

In some embodiments, the compositions of this invention will consist essentially of an active polyol ingredient, which polyol active ingredient is Xylitol as herein described. In some embodiments, the term "consisting essentially of" refers to a composition whose only active ingredient of a particular class of agents, is the indicated active ingredient, i.e. the only active polyol is Xylitol, however, other compounds may be included which are involved directly in the therapeutic effect of the indicated active ingredient. In some embodiments, with reference to the compositions of this invention, when referring to a composition consisting essentially of an active polyol ingredient, which polyol active ingredient is Xylitol, such reference specifically excludes the incorporation of more than 0.01% inorganic salt in the composition, in order to achieve a formulation exhibiting non-Newtonian shear thinning viscosity.

In some embodiments, the term "consisting essentially of" refers to a composition whose only active ingredient of targeting a particular mechanism, or acting via a particular pathway, is the indicated active ingredient, however, other compounds may be included which are involved directly in the therapeutic effect of the indicated active ingredient, which for example have a mechanism of action related to but not directly to that of the indicated agent.

For example, and representing an embodiment of this invention, the compositions of this invention consisting essentially of an active polyol ingredient, which polyol active ingredient is Xylitol may consist further of an anti-inflammatory or anti-infective agent, which agents assist in treating a joint condition, but which secondary treatment is unrelated to the effect of the Xylitol.

In some embodiments, the term "consisting essentially of" refers to a composition whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" may refer to components which facilitate the release of the active ingredient. In some embodiments, the term "consisting" refers to a composition, which contains the active ingredient and a pharmaceutically acceptable carrier or excipient.

Although the pharmaceutical compositions provided herein are principally directed to pharmaceutical compositions which are suitable for administration to humans, it will be understood by the skilled artisan that such compositions are generally suitable for administration to animals of all sorts. Modification of pharmaceutical composition suitable for administration to humans in order to render the compositions suitable for administration to various animals is well understood, and the ordinarily skilled veterinary pharmacologist can design and perform such modification with little, if any, experimentation. Subjects to which administration of the pharmaceutical compositions of the invention is contemplated include, but are not limited to, humans and other primates, and other mammals.

In some embodiments, this invention provides a method of treating a joint disease, disorder or condition, said method comprising injecting a pharmaceutical composition into an affected joint tissue, wherein said composition comprises a polyol, which polyol is xylitol and an anionic polymer, wherein said composition exhibits non-Newtonian shear thinning viscosity. In some embodiments, this invention provides for the use of a polyol, which polyol is xylitol and an anionic polymer in the manufacture of an injectable pharmaceutical formulation, formulated for intra-articular injection, which composition exhibits non-Newtonian shear thinning viscosity for the alleviation or reduction of joint irritation or for the reduction of worsening of existing joint inflammation.

In some embodiments, this invention provides a method of treating a joint disease, disorder disease, disorder or condition, said method comprising injecting a pharmaceutical composition into an affected joint tissue, wherein said composition comprises xylitol and optionally at least a second therapeutic agent, wherein said second therapeutic agent comprises an anionic polymer, an anti-inflammatory agent, an antioxidant, a vitamin, a second polyol or combinations thereof.

In some embodiments, this invention provides for the use of xylitol and optionally at least a second therapeutic agent, wherein said second therapeutic agent comprises an anionic polymer, an anti-inflammatory agent, an antioxidant, a vitamin, a second polyol or combinations thereof in the manufacture of an injectable pharmaceutical formulation, formulated for intra-articular injection, which composition exhibits non-Newtonian shear thinning viscosity for the alleviation or reduction of joint irritation or for the reduction of worsening of existing joint inflammation.

In one embodiment, the compositions of the invention may be administered acutely for acute treatment of temporary conditions, or may be administered chronically, especially in the case of progressive, recurrent, or degenerative disease. In one embodiment, one or more compounds of the invention may be administered simultaneously, or in another embodiment, they may be administered in a staggered fashion. In one embodiment, the staggered fashion may be dictated by the stage or phase of the disease.

As used herein, the term "treating" includes preventive as well as disorder remittive treatment. In some embodiments, the methods of treatment/uses of the compositions as described herein for treating a joint condition, disease or disorder, include reducing, suppressing or inhibiting the same. In some embodiments, the terms "reducing", "suppressing" and "inhibiting" have their commonly understood meaning of lessening or decreasing. In some embodiments, the methods of treatment/uses of the compositions as described herein for treating a joint condition, disease or disorder, include halting disease progression. As used herein, the term "progression" means increasing in scope or severity, advancing, growing or becoming worse. In some embodiments, the methods of treatment/uses of the compositions as described herein for treating a joint condition, disease or disorder, include preventing disease recurrence. As used herein, the term "recurrence" means the return of a disease after a remission.

As used herein, the term "administering" refers to bringing a subject in contact with a compound of the present invention. As used herein, administration can be accomplished in vitro, i.e. in a test tube, or in vivo, i.e. in cells or tissues of living organisms, for example humans. In one embodiment, the present invention encompasses administering the compounds of the present invention to a subject.

In some embodiments, the compositions, methods and/or uses of this invention provide a means for the alleviation or reduction of joint irritation and/or the alleviation or reduction of joint inflammation, and/or the alleviation or reduction of articular cartilage damage, and/or the alleviation or reduction of arthritis.

In one embodiment, "preventing, or treating" refers to any one or more of the following: delaying the onset of symptoms, reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, preventing relapse to a disease, decreasing the number or frequency of relapse episodes, increasing latency between symptomatic episodes, increasing time to sustained progression, expediting remission, inducing remission, augmenting remission, speeding recovery, or increasing efficacy of or decreasing resistance to alternative therapeutics. In one embodiment, "treating" refers to both therapeutic treatment and prophylactic or preventive measures, wherein the object is to prevent or lessen the targeted pathologic condition or disorder as described hereinabove.

In another embodiment, "symptoms" may be any manifestation of a disease or pathological condition as described hereinabove.

The administration mode of the compounds and compositions of the present invention, timing of administration and dosage, i.e. the treatment regimen, will depend on the type and severity of the disease and the age and condition of the subject. In one embodiment, the compounds and compositions may be administered concomitantly. In another embodiment, the compounds and compositions may be administered at time intervals of seconds, minutes, hours, days, weeks or more.

While the invention will now be described in connection with certain preferred embodiments in the following examples so that aspects thereof may be more fully understood and appreciated, it is not intended to limit the invention of these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of proving what is believed to be the most useful and readily understood description of formulation procedures as well as of the principles and conceptual aspects of the invention.

EXAMPLES

Example 1. Intra-Articular Injection with Hyaluronate Having Non-Newtonian Viscosity Property

| | |
|---|---|
| Hyaluronate | 1 gm |
| Xylitol | 4.5 gm |
| Water to | 100 gm | pH adjusted to about 7.0
It is to be used by single or serial injections.
It is very viscous, but because of the non-newtonian shear thinning viscosity property, it is easy to inject. It also has lubricant action.

Example 2. Intra-Articular Injection without Hyaluronate

| | |
|---|---|
| Xylitol | 4.5 gm |
| Water to | 100 gm | pH adjusted to about 7.0
It is to be used by single or serial injections.

Example 3. Intra-Articular Injection with Lipid

| | |
|---|---|
| Xylitol | 4.5 gm |
| Lecithin emulsion | 1 gm |
| Water to | 100 gm | pH adjusted to about 7.0
It is to be used by single or serial injections.
The lecithin provides lubrication.

Example 4. Intra-Articular Injection with Hyaluronate

| | |
|---|---|
| Hyaluronate | 1 gm |
| Xylitol | 3 gm |
| Buffered saline | 0.3 gm |
| Water to | 100 gm | pH adjusted to about 7.0
It is to be used by single or serial injections.

Example 5. Intra-Articular Injection with an Anti-Inflammatory Agent

| | |
|---|---|
| Xylitol | 4.5 gm |
| Methyl predinsolone acetate | 4 gm (in suspension) |

-continued

| Buffered saline | 0.3 gm |
|---|---|
| Water to | 100 gm | pH adjusted to about 7.0
It is to be used by single or serial injections.

Example 6. Intra-Articular Injection with Non-Steroidal Anti-Inflammatory Agent

| Xylitol | 3.0 gm |
|---|---|
| Diclofenac sodium | 0.3 gm |
| Buffered saline | 0.3 gm |
| Water to | 100 gm | pH adjusted to about 7.0
It is to be used by single or serial injections.

Example 7. Treatment of Arthritic or Arthrotic Joints

The knee joints of the hind legs of rabbits weighing 2-3 Kg., were injected with sterile solutions prepared according to the above examples and as described in the table below. After 24 hours the rabbits were sacrificed, the joints were removed and histological studies of the synnovial membrane were carried out.
Each of the following histological findings was scored 0 to 3.
 a. Synovial lining hyperplasia
 b. Presence of Fibrin
 c. Inflammatory infiltration
 d. Necrosis
Signs of serious irritation and inflammation by injecting 0.25 ml of 0.5% SLS were found (see Table 1). When certain compounds with 0.25 ml of 0.5% SLS were injected, alleviation of the damage to the synovial membrane was found.
Results

TABLE 1

| 0.25 ml of 0.5% SLS treatment per rabbit's knee - sacrifice 24 h after intra-articular injection | Mean | Standard error of the mean |
|---|---|---|
| Saline (negative control) | 1.4 | 0.4 |
| 0.2% SLS in saline | 1.4 | 0.3 |
| 0.5% SLS in saline (positive control) | 5.8 | 1.0 |
| 5.4% Mannitol in distilled water | 3.4 | 0.6 |
| 4.5% Xylitol in distilled water | 1.4 | 0.4 |
| 1% sodium Hyaluronate in saline | 1.0 | 0.4 |
| 0.5% SLS in 1% sodium Hyaluronate in saline | 0.8 | 0.4 |
| 0.5% SLS in 4.5% xylitol in distilled water | 0.4 | 0.8 |

SLS = sodium lauryl sulphate

Referring to the results in the above table, it will be noted that an injection of 0.5% SLS in saline gave a result of 5.8, which is the highest irritation result, while injection of only saline gave a result of 1.4 which is considered to be the norm without irritation or inflammation.

In the next to last row of the table, there is shown the results of injection 0.5% SLS in combination with 1% sodium hyaluronate in saline, which is a known anti-irritant, anti-inflammatory agent and the result is 0.8 which is not significantly different than the result for the saline negative control by itself.

As will be noted, in the last row of the table, there is shown the results of injection of 0.5% SLS in 4.5% Xylitol in distilled water, wherein the result is 0.4, which is also not significantly different than the result of the saline negative control by itself and which proves that indeed Xylitol is surprisingly effective in this context.

As will be noted from row 4 of said table, Mannitol, which has structure similar to that of Xyliltol, and which therefore would be expected to function in a similar manner, by itself in distilled water, gave a result of 3.4 showing that it does not prevent irritation, when injected by intra-articular injection into a rabbit's knee. Similarly, lack of prevention of irritation is shown by some other polyols (e.g. glycerol or glucitol) tested in comparable circumstances (data not shown).

For this reason also, it is surprising and could not be predicted that Xylitol, formulated for intra-articular injection, would be effective for the prevention of joint irritation or worsening of existing joint inflammation as a result of further irritation.

Example 8. Comparative Frictional Coefficients in Human Cartilage Samples in the Presence of Different Lubricants Human cartilage samples were obtained and a human joint friction test was conducted as described in Merkher Y. et. al., (2006) Tribology Letters 22: 29-36. The upper human cartilage sample had an approximately 4 mm diameter and the lower human cartilage sample had an approximately 6 mm diameter. Two lubricants were tested, samples 1d and 2s. 1d corresponds to a 1% sodium hyaluronate in an isotonic salt free non-Newtonian viscosity profile formulation, and 2s corresponds to a 1% sodium hyaluronate in the presence of isotonic saline, therefore being a Newtonian viscosity profile formulation. 10N of load was applied, at a speed of 1 mm/s over a distance of 4 mm, with the temperature at 36-37° C.

Table 2 describes the mean frictional dynamic and static coefficients obtained.

| | Lubricant 2s | | Lubricant 1d | |
|---|---|---|---|---|
| | Dynamic | Static | Dynamic | Static |
| Average | 0.048921 | 0/061013 | 0/037588 | 0/057958 |
| Standard Deviation | 0/013698 | 0/013623 | 0/014809 | 0/012595 |

In the presence of lubricant 2s, the cartilage samples adhered to each other much more strongly than in the presence of lubricant 1d.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. An injectable pharmaceutical formulation comprising Xylitol as an active ingredient therein, wherein the injectable pharmaceutical formulation is formulated for intra-articular injection and is portioned in vials for a single use injection or in single injections, and with the proviso that the injectable pharmaceutical formulation does not include hyaluronic acid or salts thereof, wherein the formulation is in water and sterilized, the concentration of Xylitol is between 0.5% and 10%, the formulation contains less than 0.01% of any inorganic salt and the formulation comprises at least one polymer.

2. The injectable pharmaceutical formulation according to claim 1, wherein the at least one polymer is an anionic polymer and the injectable pharmaceutical formulation is formulated to possess non-Newtonian shear thinning viscosity.

3. The injectable pharmaceutical formulation according to claim 1, wherein the injectable pharmaceutical formulation further comprises an anti-inflammatory agent or anti-infective agent or combination thereof in addition to the Xylitol for the alleviation or reduction of joint irritation or for the reduction of worsening of existing joint inflammation as a result of further irritation and is formulated for intra-articular injection in a mammalian subject.

4. An injectable pharmaceutical formulation consisting essentially of Xylitol as the active ingredient wherein the injectable pharmaceutical formulation is formulated for intra-articular injection and is portioned in vials for a single use injection or in single injections, wherein the formulation is in water and sterilized, the concentration of Xylitol is between 0.5% and 10%, the formulation contains less than 0.01% of any inorganic salt and the formulation comprises at least one polymer.

5. An injectable pharmaceutical formulation comprising Xylitol as the active ingredient therein, wherein the injectable pharmaceutical formulation is portioned in vials for a single use injection or in single injections and is formulated for intra-articular injection in a mammalian subject, and with the proviso that the injectable pharmaceutical formulation does not include hyaluronic acid or salts thereof, wherein the formulation is in water and sterilized, the concentration of Xylitol is between 0.5% and 10%, the formulation contains less than 0.01% of any inorganic salt and the formulation comprises at least one polymer.

6. The injectable pharmaceutical formulation according to claim 1, wherein the injectable pharmaceutical formulation is substantially devoid of any oil in water or wax in water emulsion.

7. The injectable pharmaceutical formulation according to claim 1, further comprising at least one pharmaceutically acceptable excipient or additive.

8. The injectable pharmaceutical formulation according to claim 1, further comprising at least one pharmaceutical agent selected from the group consisting of an anti-inflammatory agent, an antioxidant, a vitamin, another polyol, and combinations thereof.

9. The injectable pharmaceutical formulation according to claim 1, wherein the polymer is a carbomer, carboxy methyl cellulose, hydroxyl propyl methyl cellulose or polyvinyl alcohol.

10. The injectable pharmaceutical formulation according to claim 1, wherein Xylitol is the only active ingredient in the injectable pharmaceutical formulation providing anti-irritant activity.

11. The injectable pharmaceutical formulation according to claim 10, further comprising at least one pharmaceutical agent selected from the group consisting of an anti-inflammatory agent, an antioxidant, a vitamin, an anti-infective agent, another polyol, and combinations thereof.

12. The injectable pharmaceutical formulation according to claim 4, wherein Xylitol is the only active ingredient in the injectable pharmaceutical formulation providing anti-irritant activity.

13. The injectable pharmaceutical formulation of claim 1, wherein the injectable pharmaceutical formulation is portioned in vials for a single use injection.

14. The injectable pharmaceutical formulation of claim 4, wherein the injectable pharmaceutical formulation is portioned in vials for a single use injection.

15. The injectable pharmaceutical formulation according to claim 13, wherein Xylitol is the only active ingredient in the injectable pharmaceutical formulation providing anti-irritant activity.

16. The injectable pharmaceutical formulation according to claim 1, wherein the injectable pharmaceutical formulation is in a single-use syringe.

17. The injectable pharmaceutical formulation according to claim 4, wherein the polymer is a carbomer, carboxy methyl cellulose, hydroxyl propyl methyl cellulose or polyvinyl alcohol.

18. The injectable pharmaceutical formulation according to claim 5, wherein the polymer is a carbomer, carboxy methyl cellulose, hydroxyl propyl methyl cellulose or polyvinyl alcohol.

19. The injectable pharmaceutical formulation according to claim 1, wherein the formulation consists of said Xylitol, water and polymer.

20. The injectable pharmaceutical formulation according to claim 3, wherein the formulation consists essentially of said Xylitol, said anti-inflammatory agent or anti-infective agent or combination thereof, said water and said polymer.

* * * * *